(12) United States Patent
Fencl

(10) Patent No.: US 6,589,476 B1
(45) Date of Patent: Jul. 8, 2003

(54) REDUCING VOLATILE ORGANIC COMPOUNDS AND COMMON ORGANIC ODORS TO BELOW THRESHOLD LEVELS IN A MECHANICALLY VENTILATED SPACE

(75) Inventor: Forrest B. Fencl, Huntington Beach, CA (US)

(73) Assignee: Steril-Aire USA, Inc., Cerritos, CA (US)

(*) Notice: Subject to any disclaimer, the term of this patent is extended or adjusted under 35 U.S.C. 154(b) by 0 days.

(21) Appl. No.: 09/373,955

(22) Filed: Aug. 13, 1999

(51) Int. Cl.$^7$ .................................................. A61L 9/20
(52) U.S. Cl. .................. 422/4; 422/5; 422/24; 422/121
(58) Field of Search .............................. 422/24, 121, 4, 422/5

(56) References Cited

U.S. PATENT DOCUMENTS

| | | |
|---|---|---|
| 3,744,216 A | 7/1973 | Halloran |
| 4,045,316 A | 8/1977 | Legan |
| 5,334,347 A | 8/1994 | Hollander |
| 5,547,635 A * | 8/1996 | Duthie, Jr. .................... 422/24 |
| 5,612,001 A * | 3/1997 | Matschke ............... 422/121 X |
| 5,817,276 A | 10/1998 | Fencl |
| 5,866,076 A | 2/1999 | Fencl |

OTHER PUBLICATIONS

Nagle, "The How and Why of Electronic Noses," IEEE Spectrum, Sep. 1998, pp 22–34.

* cited by examiner

Primary Examiner—Elizabeth McKane
(74) Attorney, Agent, or Firm—Steven C. Sereboff; Socal IP Law Group

(57) ABSTRACT

A mechanical ventilation system, which obtains and maintains to below threshold reduced concentrations of volatile organic compounds and common organic odors in an air stream. The air stream has a concentration of volatile organic compounds of at least 100 parts per million and a temperature of between 30° and 70° F. The mechanical ventilation system comprises a duct, an air moving apparatus and a low-pressure germicidal lamp. The duct has a volume of at least five cubic feet for temporally containing and directing the air stream. The air moving apparatus moves the air stream through the duct at a speed of at least 100 cubic feet per minute. The low-pressure germicidal lamp is installed with respect to the duct such that the germicidal lamp, when energized, will irradiate the air stream passing through the duct. The germicidal lamp, when energized, produces ultraviolet radiation of approximately 254 nm with a power of at least 300 microwatts/cm2 at 1 meter for every 4 square feet of duct area, with substantially no ozone generated. Application of the ultraviolet light to the air stream reduces concentrations of volatile organic compounds and other common organic odors in an air stream to below thresholds such as ordinary olfactory detection.

16 Claims, 2 Drawing Sheets

REDUCING VOLATILE ORGANIC COMPOUNDS AND COMMON ORGANIC ODORS TO BELOW THRESHOLD LEVELS IN A MECHANICALLY VENTILATED SPACE

RELATED APPLICATION INFORMATION

This application is related to application Ser. No. 08/773,643, filed Dec. 24, 1996 entitled "Single-Ended Germicidal Lamp for HVAC Systems," issued Feb. 2, 1999 as U.S. Pat. No. 5,866,076, which is incorporated herein by reference.

This application is related to application Ser. No. 08/803,350 filed Feb. 20, 1997 entitled "Method of UV Distribution in an Air Handling System," issued Oct. 6, 1998 as U.S. Pat. No. 5,817,276, which is incorporated herein by reference.

This application is related to application Ser. No. 09/167,376 filed Oct. 6, 1998 entitled "Reduction of Energy Consumption in a Cooling or Heating System Through UVC Irradiation," which is incorporated herein by reference.

This application is related to application Ser. No. 09/170,361 filed Oct. 13, 1998 entitled "Returning a Heat Exchanger's Efficiency to 'As New,'" which is incorporated herein by reference.

This application is related to application Ser. No. 09/173,081 filed Oct. 14, 1998 entitled "Reduction of Pressure Drop of a Cooling or Heating System."

This application is related to application Ser. No. 09/172,638 filed Oct. 14, 1998 entitled "Control of Health Hazards in an Air Handler."

This application is related to application Ser. No. 09/172,637 filed Oct. 14, 1998 entitled "Cleaning and Maintaining a Drain Pan in an Air Handling System."

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure, as it appears in the Patent and Trademark Office patent files or records, but otherwise reserves all copyright and trade dress rights whatsoever.

BACKGROUND OF THE INVENTION

1. Field of the Invention

The present invention relates generally to methods and apparatus for achieving and maintaining acceptable indoor air quality.

2. Description of Related Art

One industry that is mature and economically sensitive to costs is the heating, ventilation and air conditioning (HVAC) industry. Because of the competitive nature of both the construction and HVAC industries, HVAC systems must be inexpensive to purchase and install. Of a more global interest though, is the cost to operate and maintain HVAC systems. Often, a building owner will replace an aging HVAC system as the reduction in operating and maintenance costs can offset the retrofit cost, sometimes in a matter of months.

HVAC systems are typically comprised of a cooling and heating section for, respectively, cooling and heating the air. An HVAC system will also include fans and ductwork for moving this conditioned air where it is needed. In most HVAC systems, air is drawn in, filtered, cooled and dehumidified or heated and humidified, and then delivered to a space. The greatest portion of this air is drawn from the space for recirculation through the HVAC system.

One factor impacting design and operation of HVAC systems is indoor air quality (IAQ). A major consideration in IAQ today is the amount of outdoor air introduced by an HVAC system into an otherwise sealed space. The HVAC industry and others have adopted standards for the introduction of outdoor air into spaces serviced by an otherwise closed HVAC system. These include offices, residential, commercial, industrial and institutional spaces, as modes of transportation such as cars, buses, planes and ships. In addition to controlling indoor air for occupant comfort, the goal of most HVAC systems is to provide air with reduced levels of particulate, gases and bioaerosols, be it for semiconductor, pharmaceutical or food processing facilities, hospitals, schools or offices and now the home.

Various reasons have contributed to the lack of success in utilizing germicidal lamps for bioaerosol control (IAQ), except for limited and specialized purposes. The functional implementation of such devices in air moving systems has been limited generally to expensive portable units with questionable efficacy. However, non-moving air devices can be found as wall or ceiling mount systems where the germicidal lamp is situated in a minimum air movement, and proper ambient air temperature area. A typical germicidal tube is designed to operate in still air of 80–90° F. to maintain a tube wall temperature of 105° F. Germicidal lamps have sensitive physical characteristics including plasma gas(es), mercury and partial pressures thereof.

When a conventional germicidal lamp is used to irradiate moving airstreams, the air moving across the tube removes heat and lowers the tube's temperature. The tube's mercury begins to condense such that the emission of the germicidal wavelength of 253.7 nm decreases. This decrease can be up to 75% when the tube wall temperature reaches 58° F. Also, at lower internal temperatures, tube components degrade quicker, shortening tube life. This phenomenon, known as skin effect cooling, requires a notable increase in the number of conventional tubes required for a given level of performance. Increasing the number of tubes reduces the available square area for airflow. This in turn requires the airs' velocity to increase, which decreases the dose (time times intensity) and air volume. If such a system could be made to work, it would require an increase in fan horsepower, UVC light energy and in the number of expensive tube replacements.

Conventional germicidal lamps emit ultraviolet light at both the primary and secondary emission lines of mercury (254 nm and 187 nm). At mercury's 187-nm line, ozone is created and in many applications of germicidal lamps, such as in water, this is desirable. However, ozone has strict threshold limit values in air due to its strong oxidative properties and harm to humans. Also, numerous companies have attempted to apply germicidal lamps to HVAC systems, these conventional germicidal lamps have proved unsatisfactory. Typically, a conventional germicidal lamp performs best when installed in a device or room where the air is still and/or warm. So despite the clear benefits of germicidal lamps, problems such as decreased output in moving and/or low temperature air, reduced air changes and ozone production have prevented their use in all but specialized environments.

Germicidal fixtures continue to enter the HVAC market. Recent entries have been sold under the Germ-O-Ray and Germitroll trademarks. The particular capabilities and design of these devices is not known to the inventors, though it is believed both devices use conventional tubes so that when installed in air ducts, they will suffer from the criteria outlined above.

For further information concerning improvements in electric discharge devices, which are directed to overcoming such problems, reference is made to the above-identified patent applications. These other patent applications describe excellent devices and methods for using germicidal lamps to make HVAC systems more efficient, less costly to operate and maintain, and to provide better IAQ for a healthier environment.

Germicidal tubes differ significantly from electric discharge devices used in ultraviolet gas spectroscopy (VUV tubes). Germicidal tubes are low-pressure types that emit UV light at the primary and secondary emission lines of mercury—254 nm and 187 nm. In contrast, VUV tubes are high-pressure types that operate at high temperatures and as a consequence, emit different spectral lines and intensities.

In occupant air one group of gas phase contaminants are classified as volatile organic compounds (VOCs). VOCs have been associated with simple unpleasant odors to serious maladies. Many people can detect even low part per billion (ppb) concentrations of VOCs in the air, and VOCs can be found in concentrations of parts per million (ppm). Numerous studies show the human nose to be the best gas chromatograph and further that many people have mild to serious sensitivities to certain or mixed VOCs and their associated odors. In higher concentrations, some VOCs can cause physical discomfort and maladies requiring medical attention. Since newer buildings have become more energy efficient (tighter), internally generated VOCs are of greater concern.

Some level of VOCs and other organic odors have existed in new and old buildings alike for decades. Mechanically ventilated spaces accumulate simple organic gas phase compounds as a result of operating office equipment, adding new building materials or furnishings and using various cleaning agents and solvents to name a few.

When attempting to rectify IAQ problems, gaseous contaminants can be diluted (controlled) through the introduction of outside air. However, diluting VOCs with outdoor air is neither efficient nor cost effective. It requires both more heating and cooling to condition this air and it may bring in more pollutants than it dilutes.

Other prior art methods include filtering air through activated carbon or activated alumina encapsulated by potassium permanganate, to either adsorb the VOCs or to chemically react with them in an effort to break them down (oxidize). Both of these methods have certain disadvantages. Both filtering devices require additional space and structure within the ventilation system as they can be 24"×24"×24" for every 2000 cfm and weigh over 110 pounds each. Additionally, they require added system static pressure (in air horsepower) to move air through them. Both require lots of natural resources to either reactivate or dispose of as hazardous waste fill. The initial cost to install these filters, excluding labor, is approximately $850 for every 2000 cfm. Their maintenance costs are from $290 to $400 annually. A properly designed activated carbon system lasts approximately 12 months. A properly designed potassium permanganate encapsulated activated alumina system lasts approximately 9 months. Thus, at least once per year, these special filters require expensive, hazardous and intrusive service. These systems also require more air horsepower to move air through them and thus more energy consumed. When they are added to an existing system, it could necessitate speeding up the fan and/or changing out the fan and fan motor to a larger size.

Outside of HVAC, VOC-control has been pursued through several techniques. One technique uses liquids to wash VOCs from a gas stream. However, these liquid systems are inadequate for treating air in an HVAC system. They can be more costly and hazardous than the filter systems described above. Heat treatment using radiant beds or afterburners has been used to partially catalyze VOCs in certain applications. However, heat treatment is not compatible with HVAC systems. The amount of heat that is added would also have to be offset by added cooling capacity. Photocatalysis has been gaining popularity in high VOC concentration atmospheres but again first and operating costs are prohibitive. Solvent recovery systems utilizing high volumes of activated carbon are the extreme and here we are simply dealing with a misapplication.

UVC at predominately 253.7 nm in and of itself has not been considered for VOC control. One prior art method used ultraviolet light of 185 nm to produce ozone for breaking down odor. In that prior art method, an air stream was passed across an ultraviolet lamp of UV energy at 185 nm where oxygen ($O_2$) is separated forming unstable $O_1$'s, which combine with $O_2$'s to form $O_3$'s or ozone. Also, it was found that when an ultraviolet lamp was placed in a moving airstream, the reduced UV output was insufficient enough to reduce the production of both 185 nm generated ozone and 253.7 nm UVC to have much effect on most VOCs. Thus, reliance only upon ultraviolet light even when producing ozone was considered wholly inadequate for VOC-control.

SUMMARY OF THE INVENTION

The previously described problems are solved in a method and apparatus for reducing ppb concentrations of volatile organic compounds and common organic odors to below threshold limit values in a mechanically ventilated space. The mechanically ventilated space has a mechanical ventilation system comprising plural ducts and an air moving apparatus such as a fan. Ultraviolet radiation is introduced into a duct to treat an air stream passing by the UV radiation and moving through the duct. The air stream passes at a speed of at least 100 to over 1500 feet per minute and has a temperature of between 30° and 90° F. An untreated air stream could have a concentration of volatile organic compounds as high as 100 parts per million.

A low-pressure germicidal lamp is installed with respect to the interior of the duct such that the germicidal lamp, when energized, will irradiate the air stream. The germicidal lamp when energized emits ultraviolet radiation of approximately 254 nm with a power of at least 30 to 3000 microwatts/$cm^2$ at 1 meter for every 4 square feet of duct area, with substantially no ozone generated. The UV ionization radiation separates many volatile organic compounds at the molecular and atomic level to water vapor and carbon dioxide thereby lowering the concentration of volatile organic compounds to 90 parts per million and down to 10 parts per billion.

Still further objects and advantages attaching to the device and to its use and operation will be apparent to those skilled in the art from the following particular description.

DESCRIPTION OF THE DRAWINGS

Further objects of this invention, together with additional features contributing thereto and advantages accruing therefrom, will be apparent from the following description of a preferred embodiment of the present invention which is shown in the accompanying drawings with like reference numerals indicating corresponding parts throughout and which is to be read in conjunction with the following drawings, wherein.

These and additional embodiments of the invention may now be better understood by turning to the following detailed description wherein an illustrated embodiment is described.

DETAILED DESCRIPTION OF THE INVENTION

Throughout this description, the preferred embodiment and examples shown should be considered as exemplars, rather than limitations on the apparatus and methods of the present invention.

The sun naturally produces ionizing radiation. This radiation can disturb the electrical properties of most organic compounds, and at high enough levels will break apart these organic compounds at the molecular and atomic level. The residual compounds of such broken organic compounds are mostly water vapor and carbon dioxide—harmless materials in almost any environment. Yet, for reasons suggested above, sunlight cannot be used efficiently and effectively in a mechanically ventilated space for control of VOCs. A mechanically ventilated space is defined as space which can be occupied by a person and having a mechanical ventilation system comprising plural ducts and which modifies air temperature and possibly humidity for human comfort.

The inventors have found a way to replicate sunlight's degradation of VOCs without the problems of sunlight and at a low cost. That method comprises generating specific wavelengths of ultraviolet radiation and directing that radiation into a moving air stream, which flows into the mechanically ventilated and occupied space.

Figure 1:
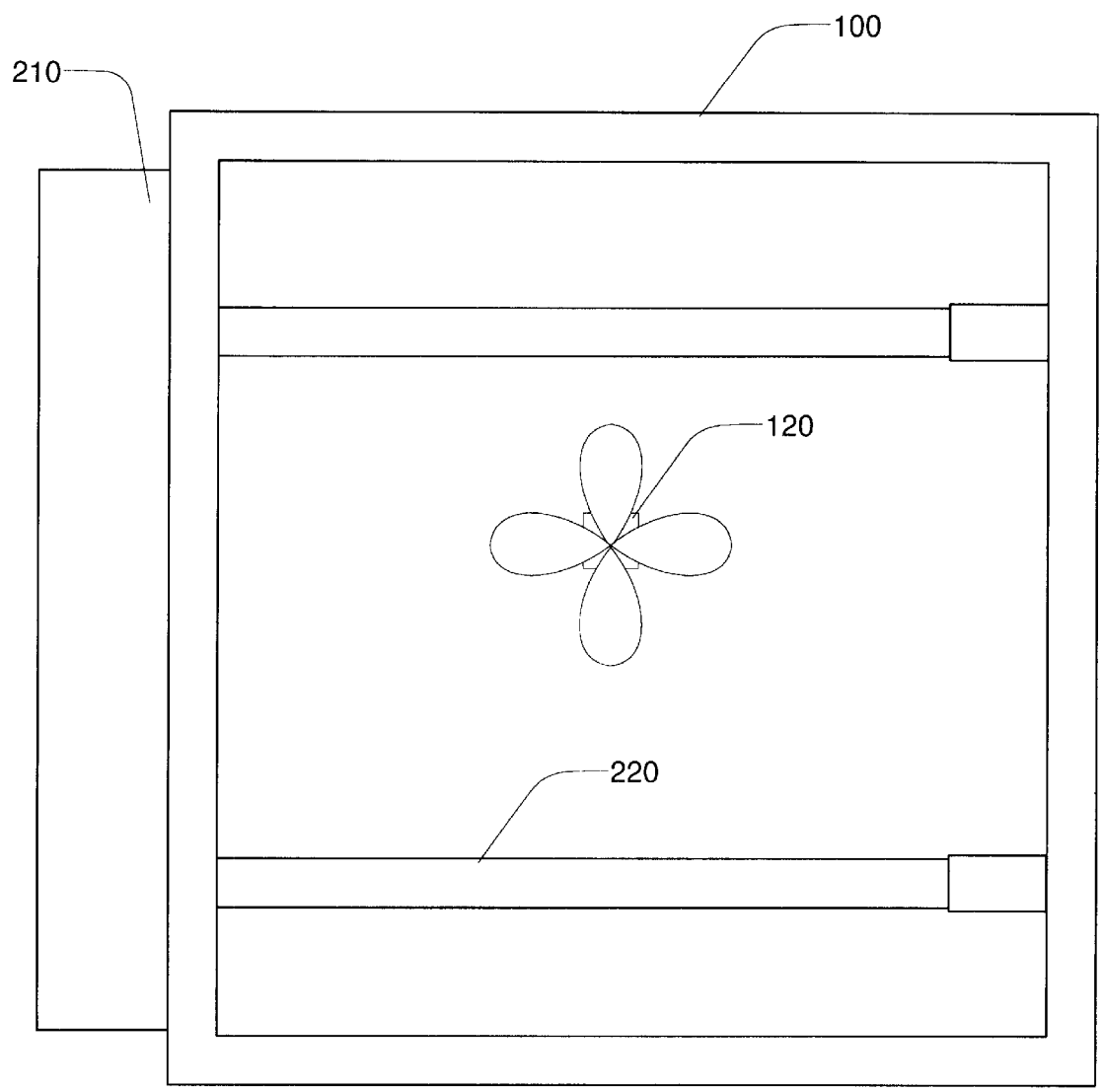
FIG. 1 is a cross section of a duct having dual, single-ended germicidal tubes installed therein.

Turning now to FIG. 1, there is shown a cross-section of a duct 100 of a mechanical ventilation system. FIG. 1 also shows a germicidal lamp 200 comprising two tubes 210 and a fixture 220. Air passing through the duct typically will have a temperature of between 30°–70° F. The humidity of this air is also typically controlled. The relatively low temperature and varying humidity render the duct a harsh environment for electronic devices, and particularly for germicidal lamps. For the germicidal lamp to operate effectively in the harsh environs of an air duct, a germicidal lamp specifically designed for such an environments must be employed. In particular, the germicidal lamps sold by the assignee of this invention, Steril-Air U.S.A., Inc, and sold under the trademark, "UVC Emitter," are preferred. These germicidal lamps produce no detectable ozone, which is also highly desirable. However, germicidal lamps which produce an insignificant quantity of ozone may be used.

The mechanical ventilation system includes an air moving apparatus. This air moving apparatus is preferably a fan 120. The fan 120 is shown in the duct 100, though the fan or other air moving apparatus may be located some distance from the germicidal lamp 200. Other air moving apparatuses which can move an air stream through the duct as described further below are within the scope of the invention.

Figure 2:
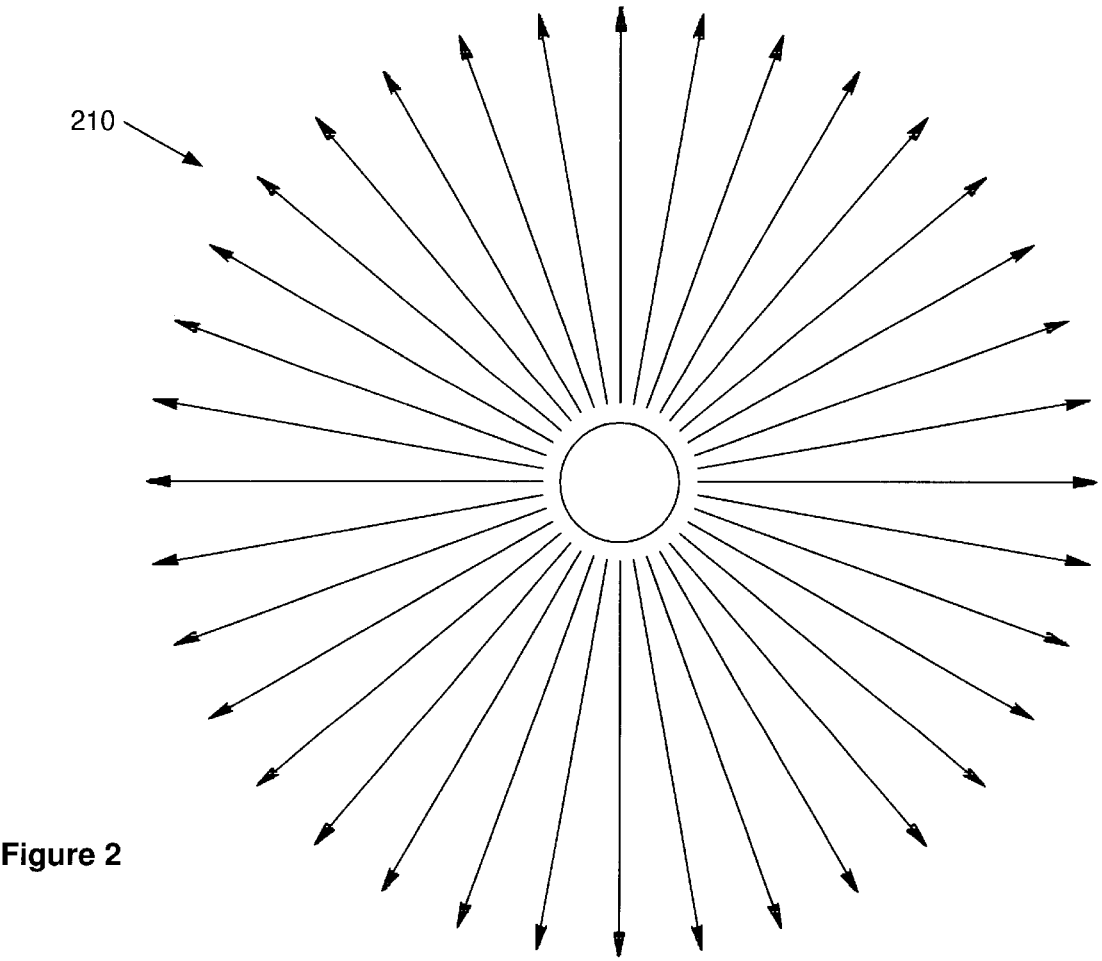
FIG. 2 is cross section of a germicidal tube in a duct and showing the radiation pattern of ultraviolet light from the tube.

In determining the spatial relationship between the germicidal tubes 210 and the walls of the duct 100, the objective is to obtain a uniform distribution of UV radiation across the duct 100. It has been determined that, for a germicidal tube which is positioned in accordance with the invention, the spatial distribution of UV radiation follows precisely that of a diffuse area source and, surprisingly, not an isotropic point source. The pattern of UV radiation from the preferred germicidal lamp is shown in FIG. 2. It can be seen that although the germicidal tube 210 is a source of radiation, the walls of the duct 100 are effectively a secondary (reflected) source of UV radiation. The diffuse radiation of the germicidal tubes 210 and diffuse reflection is therefore defined as a near field effect, not as an inverse square law. This finding is contrary to normal expectations, and therefore placement of germicidal tubes in accordance with the present invention results in the need for fewer germicidal tubes. Put another way, when the germicidal tubes 210 are positioned in sufficient proximity to the walls of the duct 100, the intensity of UV radiation from the germicidal tubes 210 at a given point is, to a degree, independent of the distance of the germicidal tubes 210 from the given point.

As shown in FIG. 2 the photons emitted from a particular point on the germicidal tube 210 radiate in all directions. Because FIG. 2 is an elevational view, the global radiation of these photons is not shown. These photons would, however, also radiate outwardly and inwardly from the plane of the paper upon which the planar representation is illustrated and from all surfaces of the tube 210.

In accordance with the invention, ultraviolet radiation from a germicidal lamp is used to reduce concentrations of VOCs and common organic odors to below threshold limit values in a mechanically ventilated space. That threshold is preferably an average person's ability to smell the VOCs and common organic odors ("olfactory detection"). To reduce VOCs and common organic odors below olfactory detection, it is believed that the concentration of VOCs must be reduced to below 100 parts per billion. The ultraviolet radiation is applied within the ductwork of the mechanical ventilation system of the mechanically ventilated space. Ultraviolet light of 254 nm will invalidate the molecular structure of a VOC in a confined airstream. A germicidal lamp is preferably used to emit ultraviolet radiation of approximately 254 nm, with substantially no ozone generated. The absence of ozone is a notable difference from most prior art methods as it is now well understood that ozone is harmful to human health and more so in the presence of certain VOCs.

In order to treat an appreciable quantity of air, the method includes directing the radiation into a relatively rapidly moving air stream. As a normal function of the operation of a mechanical ventilation system, air is passed through the system's ductwork. Preferably, the air stream has a speed of at least 100 feet per minute (FPM). More typically, the air stream has a speed of between 100 to over 1500 feet per minute. The air in the duct preferably has a temperature of between 30° and 90° F., which though not necessarily ideal for UVC type ionization of the VOCs and common organic odors, renders the method unobtrusive to operation of the mechanical ventilation system. The quality of radiation introduced into the duct is adjusted to achieve the desired results, rather than adjusting the temperature, air pressure or humidity of the air stream to be treated. This is more easily achieved with the product that the inventor offers.

The air is passed through a region of a duct having a volume of at least four cubic feet for the irradiation cited. The inventors have found that the air would have a concentration of volatile organic compounds of 100 parts per million (PPM) or less for the method to be useful.

To generate the ultraviolet radiation, a low pressure germicidal lamp, such as that shown in FIG. 1, is preferably utilized. The germicidal lamp is preferably positioned with respect to the region such that the germicidal lamp, when energized, will irradiate the region and the air stream which passes there through. The region preferably is irradiated with a power of at least 300 microwatts/cm$^2$ at 1 meter for every 4 square feet of duct area.

The germicidal lamp preferably comprises a single-ended tube and a fixture as described above. Installation of such a germicidal lamp includes producing a hole in the duct wall, mounting the fixture over the hole on the outside of the duct, inserting the tube through a hole in the fixture and in the duct wall, and securing the tube with the fixture.

The fixture preferably includes a power supply adapted to receive standard power available within the mechanical ventilation system. This typically is 115, 208/230 or 277 Vac power. Power consumption for a typical install of germicidal lamps is preferably less than 150 Watts per each 2000 CFM of duct air.

The tubes of the germicidal lamp are preferably distanced from one another such that the duct area is equally irradiated with the tube centerlines potentially based on a given concentration per unit volume of offending VOC. Because of the low power consumption of the germicidal lamps, the germicidal lamps can and should be operated at any time the mechanical ventilation system is running.

The inventors have found that, when so applied, the UV radiation destroys VOCs and common organic odors in the air stream to thereby lower the VOC concentration to as little as 10 ppb. At such a low level, the VOCs and common organic odors are beyond human olfactory detection and therefore is not a hazard or nuisance to building occupants.

In contrast to the cost and problems of the prior art methods of VOC control described above, UVC irradiation can be less costly, more predictable and as a monumental benefit, adds nothing to the environment or the space being served.

Installation of properly sized single-ended germicidal lamps requires little mechanical or physical modifications to an existing mechanical ventilation system. Thus, the method can be used in both existing and new mechanical ventilation systems, and the germicidal lamps simply added to the existing structure. The inventors have found that germicidal lamps which emit UV of approximately 254 nm without substantial ozone require relatively little energy to operate, require no changes to mechanical equipment and offer the additional benefit of killing (inactivating) microorganisms in the air.

Using UV light could reduce the amount of outdoor air for dilution or eliminate the need for adding sorbants to the air handler. The annual savings, including labor and materials for both could amount to $0.45 per CFM or more. Building owners and operators can reduce their dependency on, or eliminate the need for, increased amounts of outdoor air thus eliminating the need or requirement to condition that air for acceptable use. Additionally, productivity would be increased while absenteeism or incapacitation would be decreased. Savings in both areas would be dramatic.

Our method is especially non-evasive to the typical air handling system and can be directly related to the regenerative and restorative properties of our sun. It does not require altering the mechanical equipment to install or operate. It has lower costs of installation, operation and maintenance. It adds nothing to the airstream or environment to control gas phase compounds. It also provides a significant degree of germicidal control to further reduce absenteeism and incapacitation. Thus, the invention provides a more suitable indoor environment for occupants of any mechanically ventilated space whether at work, school or leisure.

The streams in which the above-described hydrocarbons are present as contaminants are described as conditioned spaces designed for human occupancy. Such streams typically consist of air or of rather inert gases, such as nitrogen. These gaseous hydrocarbon contaminants may be present individually or admixed in concentrations as low as 10 parts per billion (volume basis), and up to 100 parts per million. However, the present decontaminating process is sufficiently reactive to be of considerable interest even well below 100-ppb hydrocarbon concentration.

As with many chemical reactions, increased temperature generally accelerates the decontaminating process; however, the photochemical nature of the present process is rather insensitive to temperatures significantly below the thermal oxidation temperatures of the subject hydrocarbons. Consequently, temperature limitations follow from practical considerations. Similarly, the decontamination rate will increase with increased ultraviolet radiation intensity. However, it is important to control the UV so that a base intensity exists for a given concentration of VOCs. The inventors have found that an untreated tube wall will allow out the 185-nm wavelength and will generate ozone.

The pressure at which the decontamination reaction is conducted is again limited by practical considerations. The air streams of this process are subject to ordinary gas laws, and the effective residence time obtained through selection of the air speed in the duct. The decontamination reaction per se is rather insensitive to pressure within ordinary limits of 0.01 to 10 Atmospheres.

Some oxygen must be present, as ultraviolet light is believed also to react with both oxygen and background ozone to produce various activated species, including OH radicals, $O_2H_2$, $O_1$, $O_2$ and $O_3$ with excited electron states. The term "oxygen species" refers collectively to these compounds and elements and their excited allotropes. The duct is selected to provide sufficient time to oxidize or break apart the VOCs into simple products such as carbon dioxide, water vapor and hydrogen halides.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications and alterations should therefore be seen as within the scope of the present invention.

It is claimed:

1. A method of reducing concentrations of volatile organic compounds and common organic odors to below threshold limit values of human detection in a mechanically ventilated space, the mechanically ventilated space having a mechanical ventilation system comprising plural ducts, the method comprising the steps of:

(a) identifying a region having a volume of at least four cubic feet within a given duct of the mechanical ventilation system through which an air stream passes at a speed of at least 100 cubic feet per minute, the air stream having a concentration of volatile organic compounds of at least 100 parts per mission and a temperature of between 30° and 70° F.;

(b) installing a low pressure germicidal lamp with respect to the region such that the germicidal lamp, when energized, will irradiate the region and the air stream which passes there through;

(c) energizing the germicidal lamp and exposing the air stream to ultraviolet radiation of approximately 254 nm with a power of at least 300 microwatts/cm$^2$ at 1 meter for every 4 square feet of duct area, with substantially no ozone generated;

wherein the UV radiation destroys volatile organic compounds in the air stream to thereby lower the concentration of volatile organic compounds to potentially no more ten 10 parts per million.

2. The method of reducing concentrations of volatile organic compounds and common organic odors to below thresholds in a mechanically ventilated space of claim 1 wherein the air steam passes through the region of the duct at between 200 and 600 cubic feet per minutes.

3. The method of reducing concentrations of volatile organic compounds and common organic odors to below thresholds mi a mechanically ventilated space of claim 1 wherein the germicidal lamp comprises a single-ended tube and fixture, the installing step comprising:

(a) opening a hole in the duct wall;

(b) mounting the fixture over the hold on the outside of the duct;

(c) inserting the tube through a hole in the fixture and the hold in he duct wall; and (d) securing the tube to the fixture.

4. The method of reducing concentrations of volatile organic compounds and common organic odors to below thresholds in a mechanically ventilated space of claim 1, wherein the thresholds are comprised of Human olfactory detection.

5. The method of reducing concentrations of volatile organic compounds and common organic odors to below thresholds in a mechanically ventilated space of claim 1, wherein the thresholds are less than 100 parts per million.

6. A method capable of controlling low levels of volatile organic compounds (VOCs) and common organic odors in an air flow and capable of operation at ambient and cool temperatures comprising:

(a) passing the contaminated air flow through a duct, the air flow having a speed of a least 100 cubic feet per minute, the air flow having a concentration of volatile organic compounds of at least 100 parts per million and a temperature of between 30° and 70° F.;

(b) generating ultraviolet light of approximately 254 nm without generating a substantial quantity of ozone;

(c) directing the generated ultraviolet light into the duct with a power of at least 300 microwatts/cm$^2$ at 1 meter for every 4 square feet of duct area, with substantially no ozone generated;

(d) converting with the ultraviolet light the VOCs into non-toxic materials;

wherein organic gas phase compounds are degraded to below threshold limit values.

7. The method of controlling low levels of VOCs and common organic odors in an air flow of claim 6 wherein the ultraviolet light is generated by a germicidal lamp, the lamp consisting of a tube and a fixture, the duct having an inside and an outside, the method further comprising the steps of:

installing the fixture on the outside of the duct;

installing the tube into the fixture, wherein the tube extends into the duct.

8. The method of controlling low levels of VOCs and common organic odors in an air flow of claim 6 wherein the air comprises at least 5% oxygen.

9. The method of controlling low levels of VOCs and common organic odors in an air flow of claim 6 wherein the air comprises at least 25% nitrogen.

10. The method of controlling low levels of VOCS and common organic odors in an air flow of claim 6 wherein the amount of ultraviolet light directed into the duct is varied in relation to the anticipated concentration of VOCs in the air flow.

11. The method of controlling low levels of VCs and common organic odors in an air flow of claim 10 wherein the ultraviolet light is generated by a germicidal lamp, and the amount of ultraviolet light directed into the duct is varied by varying the intensity of ultraviolet light source.

12. The method of controlling low levels of VOCs and common organic odors in an air flow of claim 11 wherein the contaminant is a member selected from a group consisting of.

(a) aliphatic and aromatic hydrocarbons in a family commonly found indoors;

(b) saturated and unsaturated hydrocarbons containing 2–8 carbon atoms;

(c) halogen-substituted saturated and unsaturated hydrocarbons containing 2–8 carbon atoms, and (d) partially oxidized variants of the hydrocarbons and the halogen-substituted hydrocarbons.

13. A mechanical ventilation system which obtains and maintains to below threshold values of human detection reduced concentrations of volatile organic compounds and common organic odors in an air stream, the air stream having a concentration of volatile organic compounds of at least 100 parts per million and a temperature of between 30° and 70° F., the mechanical ventilation system comprising:

(a) a duct having a volume of at least four cubic feet for temporally containing and directing the air steam, the duct comprising at least one wall which is air-tight and defining an interior through which the air stream passes and an exterior:

(b) an air moving apparatus for moving the air stream through the duct at a speed of at least 100 cubic feet per minute:

(c) a low pressure germicidal lamp installed with respect to the duct such that the germicidal lamp when energized, will irradiate the air stream passing through the duct to lower the concentrations of volatile organic compounds and common organic odors in the air stream with substantially no ozone generated, wherein the germicidal lamp comprises:

a fixture disposed exterior to the duct; and a single-ended tube substantially disposed within the duct and electrically connected to the fixture and supported by the fixture, (d) wherein the germicidal lamp, when energized, produces ultraviolet radiation of approximately 254 nm with a power of at least 300 microwatts/cm$^2$ at 1 meter for every 4 square feet of duct area.

14. The mechanical ventilation system of claim 13 wherein the air moving apparatus moves the air stream through the duct at between 200 and 600 cubic feet per minute.

15. The mechanical ventilation system of claim 13, wherein the threshold limit values are comprised of concentrations specific to the compound that produces human olfactory detection.

16. The mechanical ventilation system of claim 13, wherein the threshold limit values comprise 10 parts per billion.

* * * * *

UNITED STATES PATENT AND TRADEMARK OFFICE
CERTIFICATE OF CORRECTION

PATENT NO.    : 6,589,476 B1                                               Page 1 of 1
DATED         : July 8, 2003
INVENTOR(S)   : Forrest B. Fencl It is certified that error appears in the above-identified patent and that said Letters Patent is hereby corrected as shown below:

Column 9,
Line 15, "steam" should be -- stream --.
Line 19, "mi" should be -- in --.

Column 10,
Line 33, "steam" should be -- stream --.
Line 64, "10" should be -- 100 --.

Signed and Sealed this

Twenty-eighth Day of October, 2003

JAMES E. ROGAN
*Director of the United States Patent and Trademark Office*